United States Patent
Brisson et al.

(10) Patent No.: US 6,757,582 B2
(45) Date of Patent: Jun. 29, 2004

(54) METHODS AND SYSTEMS TO CONTROL A SHAPING TOOL

(75) Inventors: Gabriel Brisson, Pittsburgh, PA (US); Takeo Kanade, Pittsburgh, PA (US); Anthony DiGioia, III, Pittsburgh, PA (US); Branislav Jaramaz, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 10/427,093

(22) Filed: Apr. 30, 2003

(65) Prior Publication Data

US 2003/0208296 A1 Nov. 6, 2003

Related U.S. Application Data

(60) Provisional application No. 60/377,695, filed on May 3, 2002.

(51) Int. Cl.[7] .............................................. G06F 19/00
(52) U.S. Cl. .......................... 700/186; 83/768; 606/128
(58) Field of Search ................................ 700/186, 163, 700/159, 245; 606/128; 318/568.11; 144/3.1; 83/76.8, 367, 370; 451/5

(56) References Cited

U.S. PATENT DOCUMENTS

| | | | | | |
|---|---|---|---|---|---|
| 4,660,573 A | * | 4/1987 | Brumbach | ................... | 606/128 |
| 5,449,363 A | * | 9/1995 | Brust et al. | ................. | 606/128 |
| 6,097,168 A | * | 8/2000 | Katoh et al. | ........... | 318/568.11 |
| 6,501,997 B1 | * | 12/2002 | Kakino | ....................... | 700/159 |
| 6,520,228 B1 | * | 2/2003 | Kennedy et al. | ............. | 83/76.8 |

* cited by examiner

Primary Examiner—Albert W. Paladini
(74) Attorney, Agent, or Firm—Kevin A. Oliver; Foley Hoag LLP

(57) ABSTRACT

A method and system for providing control that include providing a workpiece that includes a target shape, providing a cutting tool, providing a 3-D image associated with the workpiece, identifying the target shape within the workpiece image, providing a 3-D image associated with the cutting tool, registering the workpiece with the workpiece image, registering the cutting tool with the cutting tool image, tracking at least one of the workpiece and the cutting tool, transforming the tracking data based on image coordinates to determine a relationship between the workpiece and the cutting tool, and, based on the relationship, providing a control to the cutting tool. In one embodiment, the workpiece image can be represented as volume pixels (voxels) that can be classified and/or reclassified based on target shape, waste, and/or workpiece.

65 Claims, 13 Drawing Sheets

FIGURE 4A

| | | | | | | | |
|---|---|---|---|---|---|---|---|
| 1120 | | 1120' | | 1132'' | 1132'' | 1102' | |
| | | | | 1132'' | 1122'' | | |
| 1132 | 1132 | 1132 | 1132 | 1132 | 1122 | 1122 | |
| 1122 | 1122 | 1122 | 1122 | 1122 | 1122 | | |
| 1122 | 1122 | 1122 | 1122 | 1122 | 1122 | 1122 | 1122 |
| 1134 | 1134 | 1134 | 1134 | 1134 | 1134 | 1134 | 1134 |
| 1104 | | 1104 | | 1104 | | 1104 | |

FIGURE 4B

|  | 1132 | 1132 | 1122 |
|---|---|---|---|
| 1130 | 1132 | 1122 | |
|  | 1132 | 1122 | 1122 |
|  | 1132 | 1122 | |
| 1110' 1110' 1110' 1110' | 1132 | 1122 | 1122 1122 |
| 1134 1134 1134 1134 | 1134 1134 | 1134 1134 | |
| 1104 | 1104 | 1104 | 1104 |

FIGURE 4C

METHODS AND SYSTEMS TO CONTROL A SHAPING TOOL

CROSS-REFERENCE TO RELATED APPLICATION

This application claims benefit of priority to U.S. Provisional Patent Application Serial No. 60/377,695, filed May 3, 2002, the contents of which are herein incorporated by reference in their entirety.

FIELD

This disclosure relates generally to controls, and more specifically to controlling a tool for shaping a workpiece.

BACKGROUND

A wide variety of applications call for objects to be formed from general workpieces, where the object formation can include cutting the object from the workpiece. The precision required of the cut may depend on the particular application.

One application that can call for high precision is the shaping of bone during surgery. For example, in a surgery such as a total knee replacement (TKR), the bones to which a prosthetic knee may be attached, typically the femur and the tibia, can be shaped to facilitate stable and effective implantation of the prosthesis.

Some cutting systems achieve increased accuracy by fixating the workpiece, such as bone. Bone fixation can be accomplished using a screw(s) and/or a clamp(s) to secure the bone to a secure positioning brace. Fixation can be used for many robotic orthopedic surgery systems because such systems depend on a fixed target and cannot or do not track the target. Fixation may be used in robotic systems despite the risks to the patient that can include pain, infection, and increased recovery and rehabilitation periods caused by the invasive nature of fixation.

Robotic and other surgical systems may be susceptible to failure that can occur suddenly and can cause damage or injury to the subject. Controllable or detectible failure may be detected before harm is done. Undetectable failure may cause damage when the system appears to be functioning normally. If a robot provides power drive or power assistance to an operator, failure may result when the robot malfunctions because the operator may be unable to react in time or with sufficient force to prevent the robot components from injuring the subject. Robotic systems may also be undetectable failures, since the operator may not be in full or even partial physical control of the robot.

SUMMARY

The disclosed methods and systems include a control method that includes providing a workpiece that includes a target shape, providing a cutting tool, providing a 3-D image associated with the workpiece, identifying the target shape within the workpiece image, providing a 3-D image associated with the cutting tool, registering the workpiece with the workpiece image, registering the cutting tool with the cutting tool image, tracking the workpiece and/or the cutting tool, transforming the tracking data based on image coordinates to determine a relationship between the workpiece and the cutting tool, and based on the relationship, providing a control to the cutting tool. The control can include an analog signal, a digital signal, a control to at least partially retract a cutting element associated with the cutting tool, a control to reduce the speed of a cutting element associated with the cutting tool, a control to stop a cutting element associated with a cutting tool, or another control.

The methods and systems can include representing the workpiece image using volume pixels (voxels), and classifying the workpiece image voxels based on the target shape. Accordingly, based on the relationship between the cutting tool and the workpiece, the methods and systems can include re-classifying the voxels based on the relationship.

The methods and systems can include providing an image based on CT scan data, X-ray data, MRI data, fluoroscopy data, and/or ultrasound data. The methods and systems can also include classifying such image data, represented as three dimensional volume pixels or "voxels," where classifying the image voxels based on the target shape includes distinguishing target shape voxels and workpiece voxels. In an embodiment, distinguishing target and workpiece voxels includes associating target shape voxels with the target shape and associating non-target shape voxels as waste. Color-coding voxels, such as target shape voxels associated with the target shape, can also be performed to distinguish voxels. The images and/or voxels can be displayed to a user to enable a user to view relative positions of the cutting tool and workpiece and/or target shape. In one embodiment, the methods and systems can include re-classifying the voxels based on the relationship.

Classifying and/or re-classifying voxels can include identifying mixture voxels that include part workpiece and part target shape, subdividing the mixture voxels, and iteratively identifying and subdividing mixture voxels to a predetermined voxel resolution. In one embodiment, mixture voxels can be understood to be voxels that can be associated with more than one classification, where exemplary voxel classifications can include target, workpiece, waste, empty, cutting tool, cutting element, or other classifications. Subdividing the mixture voxels can be performed based on an octree data structure. Further, the methods and systems can include recombining voxels having the same classification, where such recombining can generally be performed based on neighboring voxels of the same classification.

The methods and systems can also include a probe that can be calibrated and employed to register the workpiece and/or the cutting tool to the workpiece image and the cutting tool image, respectively. The disclosed tracker can include a tracking method and system based on providing one or more markers on or otherwise associated with the workpiece and/or the cutting tool. The tracker can measure and/or determine at least one position and at least one angle associated with the workpiece and/or the cutting tool, where in one embodiment, the tracker can track in three positions and three angles to provide six degrees of freedom. The tracked data can thus be transformed to an image coordinate system to allow an updating of the respective image positions, angles, etc.

The image updating can also include (re)classifying voxels associated with the workpiece, where the reclassification can be based on the tracking data associated with the workpiece and/or the cutting tool. Such classifying and/or reclassifying can include identifying voxels associated with the workpiece that are eliminated by the cutting tool. The classifying and/or reclassifying can also include identifying mixture voxels, subdividing the mixture voxels, and, iteratively identifying and subdividing mixture voxels until reaching a predetermined voxel resolution. As provided previously, identifying mixture voxels includes identifying voxels having more than one classification. The subdividing can be based on an octree data structure. Voxel recombination of voxels having the same classification can also be performed.

Accordingly, the methods and systems include providing a control based on determining a distance between the cutting tool image and the voxels classified based on the target shape. In one embodiment, the control can be based on increasing the size of the cutting tool image to determine whether the increased size cutting tool intersects with the target image. The cutting tool image can be increased by a fixed amount, and/or based on tracking data associated with the cutting tool. The control provided to the cutting tool can thus be based on the relationship between a cutting element associated with the cutting tool image, and voxels classified based on the target shape.

In an embodiment, the control provided to the cutting tool can be based on the relationship between the cutting tool image and the voxels classified and/or associated with the target shape, where the relationship can be based on collision detection and/or intersection detection between at least part of the cutting tool and voxels associated with the target shape.

In one embodiment, the workpiece image can be understood to be associated with voxels that can be further associated with a three-dimensional grid of voxels, where an image associated with the workpiece can be incorporated into the grid, and grid voxels can be identified as being associated with the workpiece. Some of the workpiece voxels can thus further be associated with the target shape.

The methods and systems include providing a control to the cutting tool by performing at least one of collision detection and intersection detection. Such control can performing at least one of collision detection and intersection detection between at least part of the cutting tool and the target shape of the workpiece image.

In the disclosed methods and systems, identifying the target shape includes classifying voxels associated with the workpiece image as at least one of workpiece and target shape. Accordingly, providing control to the cutting tool can include performing at least one of collision detection and intersection detection between at least part of the cutting tool and the target shape voxels. Providing control can also include providing a control based on a threshold distance between the workpiece image and the cutting tool image.

Also disclosed is a system that includes a cutting tool, a workpiece that includes a target shape, a tracker to provide tracking data associated with the cutting tool and the workpiece, and a controller to control the cutting tool based on the tracking data associated with the cutting tool and the tracking data associated with the workpiece. The cutting tool can include one or more cutting elements that can include one or more blade(s), one or more rotatable blade(s), one or more retractable blade(s), one or more water jet(s), one or more particulate jet(s), one or more lithotriptor(s) and/or one or more ultrasonic lithotriptor(s). The controller can control the cutting tool by providing a control to at least partially retract the cutting element(s), and/or at least partially reduce a rotation rate and/or change a cutting rate of the cutting element(s). The controller can transmit a control signal to the cutting tool, where the control signal includes an analog signal, a digital signal, and no signal.

The systems can include a tracker that includes or otherwise provides tracking data based on at least three positions and at least three angles. The tracker can include one or more first markers associated with the workpiece, and one or more second markers associated with the cutting tool. The markers or some of the markers can be one or more infrared sources, Radio Frequency (RF) sources, ultrasound sources, and/or transmitters. The tracker can thus be an infrared tracking system, an optical tracking system, an ultrasound tracking system, an inertial tracking system, a wired system, and/or a RF tracking system.

The systems also include one or more images associated with the workpiece and at least one image associated with the cutting tool. The workpiece image(s) can be registered to the workpiece, and the cutting tool image(s) can be registered to the cutting tool. Accordingly, the systems include a means to register the workpiece to the image(s) associated with the workpiece, and a means to register the cutting tool to the image(s) associated with the cutting tool. The registration means can include a probe that can be calibrated prior to registration. Registration can be performed by contacting locations on the workpiece and/or cutting tool with the calibrated probe.

The systems thus also include means to provide at least one image associated with the workpiece, and means to provide at least one image associated with the cutting tool. Such means can include Computer Aided Design (CAD), CT scan, MRI data, X-ray, fluoroscopy, and/or ultrasound, although other means can be used. The systems can update the images with tracking data using means to transform the tracking data between different coordinate systems. Such transformations can be mathematically effectuated.

The systems and methods can be applied to a workpiece that includes bone, cartilage, tendon, ligament, muscle, connective tissue, fat, neuron, hair, skin, a tumor, and an organ. The cutting tool can include an endoscopic instrument.

The controller can also include a collision detection module and/or an intersection detection module that can determine a relationship between the cutting tool and at least part of the workpiece.

Disclosed is a system that includes a workpiece having a target shape included therein, a tracker to track at least one of a cutting tool and the workpiece, and, a control system, the control system including instructions to cause a processor to track the cutting tool and the workpiece, to determine a relationship between the cutting tool and at least one of the workpiece and the target shape, and to provide a control to the cutting tool based on at least one of the relationship of the cutting tool and the workpiece, and the relationship of the cutting tool and the target shape. The control system can also include an image associated with the workpiece and an image associated with the cutting tool. The image associated with the workpiece can includes an image associated with the target shape, and/or at least part of the workpiece image can be designated and/or otherwise classified as being associated with the target shape.

The system also includes an image registration means, where the image registration means registers the workpiece to an image associated with the workpiece, and the image registration means registers the cutting tool to an image associated with the cutting tool, and wherein the control system includes instructions to update at least positions of the workpiece image and the cutting tool image based on data from the tracker; and, where at least one of the relationship of the cutting tool and the workpiece, and the relationship of the cutting tool and the target shape, are based on the updated image positions.

In the disclosed systems, the relationship between the cutting tool and the workpiece can be based on position data and/or angle data associated with the cutting tool(s) and/or the workpiece, where the position data and angle data can be based on the tracker. The relationship between the cutting tool and the target shape can thus be based on position data and/or angle data associated with the cutting tool and/or the target shape, where the position data and angle data are based on the tracker. The instructions to determine a relationship between the cutting tool and the target shape and/or workpiece can also include instructions to represent the workpiece as a group of volume pixels (voxels), classify voxels corresponding to the target shape, represent the cutting tool as a group of voxels, a surface model, and/or using constructive solid geometry or other geometric modeling, and, based on the tracker data, classify and/or update the voxels. The instructions to classify voxels corresponding to the target shape can include classifying voxels as target shape and classifying voxels as waste, and/or instructions to color-code voxels corresponding to the target shape. In an embodiment, the workpiece can be represented as a surface model The disclosed methods and systems can include a control for a shaping tool that can be referred to herein as a cutting tool, and in one embodiment, is a freehand shape cutter, but can be understood to be a tool that can cut, shave, and/or grind. References herein to a shaping tool or cutting tool can accordingly be understood to represent a tool that can cut, shave, and/or grind.

The disclosed methods and systems include a freehand shape cutter that includes a handheld cutting tool having a cutting element and a first marker. A second marker can be affixable to a workpiece that includes a target shape. A tracker can track a position of the cutting tool based on a position of the first marker, and also track a position of the workpiece based on a position of the second marker. A controller can control the cutting element based on the position of the cutting tool and the position of the workpiece to prevent the cutting element from invading the target shape.

In one exemplary embodiment, the methods and systems include a method of shaping a bone by determining a target shape of the bone, aligning the target shape with the bone, providing a handheld cutting tool having a cutting element, tracking the bone and the cutting tool, cutting the bone with the cutting tool, and controlling the cutting element to prevent invasion of the cutting tool on the target shape. In such an embodiment, the target shape of the bone can be determined by creating a bone model based on geometrical data of the bone, and establishing the target shape based on the bone model.

In one embodiment, the cutting tool can have six degrees of freedom, and the tracker can track with six degrees of freedom.

The cutting element can include at least one of a blade, a rotatable blade, a retractable blade, a water jet, a particulate jet, a lithotriptor, and an ultrasonic lithotriptor. The controller can control the cutting element by at least one of stopping the cutting element, retracting the cutting element, progressively retracting the cutting element, switching off the cutting element, and interrupting power to the cutting element. The tracked and/or determined positions can be three-dimensional positions that can be tracked substantially simultaneously. Additionally and optionally, the positions can be tracked continuously.

The target shape may be represented in the controller as a virtual template. The workpiece can include, for example, at least one of bone, cartilage, tendon, ligament, muscle, connective tissue, fat, neuron, hair, skin, tumor, and an organ that can include skin, brain, meninges, palate, tongue, esophagus, stomach, duodenum, jejunum, ileum, colon, liver, kidney, spleen, pancreas, ganglion, heart, artery, vein, arteriole, venule, capillary, lung, trachea, bronchus, bronchiole, alveolus, blood, extremity, and a reproductive organ. A tumor can include a neoplasm, a benign tumor, a hyperplasia, a hypertropy, a dysplasia, an anaplasia, a metaplasia, a metastasis, and a malignant tumor.

BRIEF DESCRIPTION OF THE FIGURES

FIGS. 4A–4C provide schematic diagrams of embodiments of voxellation;

DETAILED DESCRIPTION

To provide an overall understanding, certain illustrative embodiments will now be described; however, it will be understood by one of ordinary skill in the art that the systems and methods described herein can be adapted and modified to provide systems and methods for other suitable applications and that other additions and modifications can be made without departing from the scope of the systems and methods described herein.

Unless otherwise specified, the illustrated embodiments can be understood as providing exemplary features of varying detail of certain embodiments, and therefore, unless otherwise specified, features, components, modules, and/or aspects of the illustrations can be otherwise combined, separated, interchanged, and/or rearranged without departing from the disclosed systems or methods.

The disclosed systems and methods include a methods and systems for controlling a cutting tool. In one embodiment, the cutting tool can be controlled relative to a workpiece and/or an object (target) that can be derived from the workpiece. Although the illustrated embodiments and other examples provided herein relate to surgical applications where the workpiece can be, for example, a bone, those of ordinary skill in the art will recognize that the disclosed methods and systems relate to a system and method where a target shape can be developed from other workpieces, where the workpiece can include a material including, for example, wood, plastic, living tissue, ceramic, plaster, or other non-living materials. For surgical applications, workpieces can include, for example, living tissue including bone, cadaveric grafts, or engineered tissue grafts.

The disclosed methods and systems thus include and/or can be associated with a workpiece from which a target shape can be formed using a cutting tool to cut, grind away, or otherwise eliminate pieces or portions of the workpiece. When appropriate cuts are made and pieces or portions appropriately eliminated, the remaining workpiece can be substantially similar to the desired target shape. Accordingly, the workpiece can be understood to include a target shape and waste, wherein the cutting tool can be used to eliminate the waste from the workpiece to leave the target shape. The disclosed methods and systems can thus include generating one or more computer models and/or a workpiece image that includes the target shape and a cutting tool image, registering the workpiece and the cutting tool to the respective computer models and/or images, and facilitating target shape formation by tracking the cutting tool (and/or the cutting element) and the workpiece relative to the computer models and/or images to enable the cutting tool (and/or cutting element) to cut and/or eliminate those portions of the workpiece that are not part of the target shape. A 2D representation of the 3D images can be provided on a display.

Figure 1:
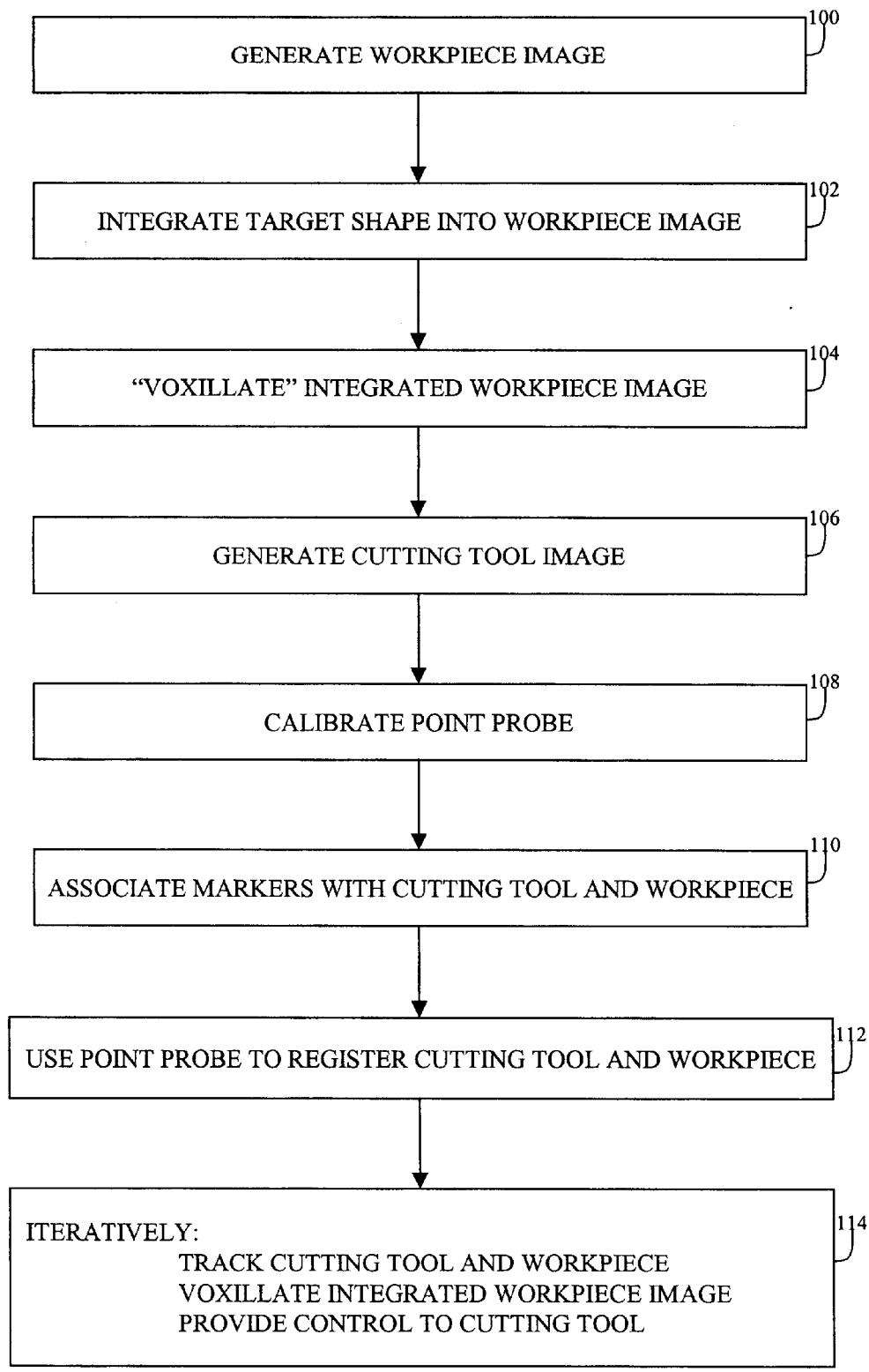
FIG. 1 is a block diagram of one embodiment.

A block diagram describing the features of a method and system as disclosed herein can be as provided in FIG. 1. As previously provided, the features of FIG. 1 are not provided in particular order, include varying levels of detail for certain embodiments, and such features are presented for illustrative purposes. Accordingly, the illustrated features of FIG. 1 can be rearranged in terms of order, and as described herein, some features can be further detailed and/or eliminated in some embodiments.

As FIG. 1 indicates, a workpiece image can be provided or otherwise generated 100 for input to a processor-controlled device that can include, and can be referred to herein, as a computer. In some embodiments, the workpiece image can be a three-dimensional (3-D) image and/or can be translated to a 3-D image for presentation. Some embodiments allow the workpiece image to be manipulated on the display screen by a computer user using keyboard, joystick, mouse, audio, and/or other commands. For example, in medical applications, the 3-D image can be provided by a Computer Aided Design (CAD), Computed Tomography (CT) Scan, Medical Resonance Imaging (MRI), and/or combinations of such data and/or other data that can include X-Ray, digital image, or other data and/or data formats. In an embodiment, a 3-D image can be provided by a 3-D wire model derived from orthogonal projections of an object, as described for example in Zdravkovic and Bilic, "Computer-assisted preoperative planning (CAPP) in orthopedic surgery," Computer Methods and Programs in Biomedicine, 32 (1990) 141–146. The computer can include a display and instructions for the processor that can cause a 2-D representation of the workpiece image to be presented on the display.

Once the workpiece image is provided 100, a target shape can be integrated into the workpiece image 102. In some embodiments, the target shape can also be a 3-D image that can be integrated with the workpiece image, or the workpiece image may merely be modified to include designations of those image portions that are target shape, and those portions which are not target shape. For the purposes of the present disclosure, non-target shape areas of the workpiece can be referred to herein as "waste." One method of generating an integrated workpiece/target shape is provided in U.S. Pat. No. 6,205,411, the contents of which are herein incorporated by reference.

Once the integrated workpiece/target image exists 102, the integrated image can be "voxellated." The term "voxellated" as provided herein, can include a method for subdividing an image into three-dimensional (3-D) pixels, or "voxels," where initially, the integrated image can be divided into voxels having resolution of, for example, 0.3 millimeters in each of three dimensions, although such resolution is merely for illustration and not limitation, and voxel resolution can depend on the embodiment and can depend, for example, on resolutions provided by a tracker for the disclosed methods and systems.

In some embodiments, the voxel size and/or dimensions can match the cutting tool tracking system accuracy, while in other embodiments, the voxel size can be an integer or fractional multiple of the tracking system accuracy and/or resolution. Accordingly, workpiece image data may be resampled to provide voxels having a desired dimension for compatibility with a tracking system.

In one illustrative embodiment, a CT scanner may provide a workpiece image having a resolution of 1 mm×1 mm×1 mm, while a tracking system may have a tracking accuracy of 0.3 mm×0.3 mm×0.3 mm. Accordingly, in one embodiment where the voxel size is the same as the tracking system accuracy and/or resolution, the integrated workpiece image can be resampled to provide voxels of size 0.3 mm×0.3 mm×0.3 mm. One illustrative tracking system can be the OPTOTRAK® 3-D motion and position measurement and tracking system described herein, although those of ordinary skill in the art will recognize that other tracking systems of other accuracies and/or resolutions can be used.

Voxellation can also provide a uniformity to an integrated image of non-uniform resolution. For example, a CT image from which an integrated image may be based, may have varying resolution and can be resampled through voxellation to provide uniformity. Such uniformity can reduce the computational burden of manipulating images because the voxels have a known and unvarying size.

Those of ordinary skill in the art will recognize that disclosed methods and systems also can also include, as provided herein, interchanging the integration and voxellation of FIG. 1, such that a workpiece image and/or a target image/shape can be voxellated, and thereafter integrated.

Referring again to FIG. 1, an image 106 of the cutting tool can also be provided to the computer. As with the workpiece, such image can be provided in a variety of methods that can include CT or other imaging system. The cutting tool image can also be voxellated in some embodiments.

For an embodiment according to FIG. 1, a point probe can be calibrated 108 using a calibration fixture that can provide, for example, accuracies on the order of 0.1 millimeter and 0.1 degree. For such a system, once the probe is calibrated 108, the probe can be used to provide discrete points on the workpiece and the cutting tool.

In one embodiment, the point probe can be calibrated using a tracking system such as the commercially available OPTOTRAK® 3-D motion and position measurement and tracking system that can be integrated with a computer such as the computer provided herein, and can provide 3-D tracking data for rigid bodies such as the workpiece, cutting tool, and probe by utilizing one or more cameras to track light-emitting diode (LED) markers located on the rigid body(s), where the LEDs can provide infrared signals that can be, in some embodiments, provided in a pattern associated with the rigid body to which the LEDs are associated. Those of ordinary skill in the art will recognize that such a tracking system is merely one illustrative tracking system, and other tracking systems and mechanisms capable of tracking a rigid body can be used without departing from the scope of the methods and systems herein.

For the OPTOTRAK® embodiment, the LED sensors can provide measurements at a rate of sixty times per second, although such measurement rate is dependent upon the application, processing power, desired tracking accuracy, anticipated refinement of computation, and other concerns. Accordingly, such sensor update rate is merely illustrative. Furthermore, other sensors besides the LED sensors can be used.

LED or other markers can be associated with or otherwise affixed to the workpiece and the cutting tool 110, and the calibrated probe can be used to measure discrete positions along the surfaces of the actual cutting tool and the workpiece (i.e., a probe user can touch the probe to the surfaces). The discrete point positions can be expressed relative to the marker and registered with the (integrated) workpiece image and cutting tool image, respectively 112. Accordingly, the methods and systems herein can thereafter relate and/or associate the workpiece to the workpiece image, the cutting tool to the cutting tool image, and by tracking the workpiece and the cutting tool, transform the tracked positions of the cutting tool and the workpiece to the images of the cutting tool and the workpiece, respectively, to allow the processor to determine whether the cutting tool is impinging upon or otherwise invading the target shape.

In an embodiment, the cutting tool and workpiece tracking can be performed independently, with independent sensors. In other embodiments, a single sensor may be used to assist tracking of the two objects. Furthermore, although the OPTOTRAK system includes an embodiment where the LED markers can be affixed to the rigid bodies to be tracked, other markers (and/or sensors) can be used that may not required such affixing. Those with ordinary skill in the art will recognize that the markers, calibration methods, and tracking methods provided herein are merely illustrative, and other methods of finding coordinates on the workpiece and/or cutting tool surface can be used, including for example, ultrasound, fluoroscopic imaging, optical range sensors, mechanical arms, etc. Furthermore, registration techniques including fiducial markers can be used.

Returning to FIG. 1, once the (integrated) workpiece image and cutting tool image are registered, respectively, to the workpiece and the cutting tool, the disclosed methods and systems can iteratively track the workpiece and the cutting tool, transform the tracked coordinates to the image coordinates, update the image(s) based on the new coordinates, and compute and transmit a control signal to the cutting tool, where the control signal can be a signal to stop, retract, continue, or reduce speed, where such control can be based on the cutting tool characteristics.

Figure 2A:
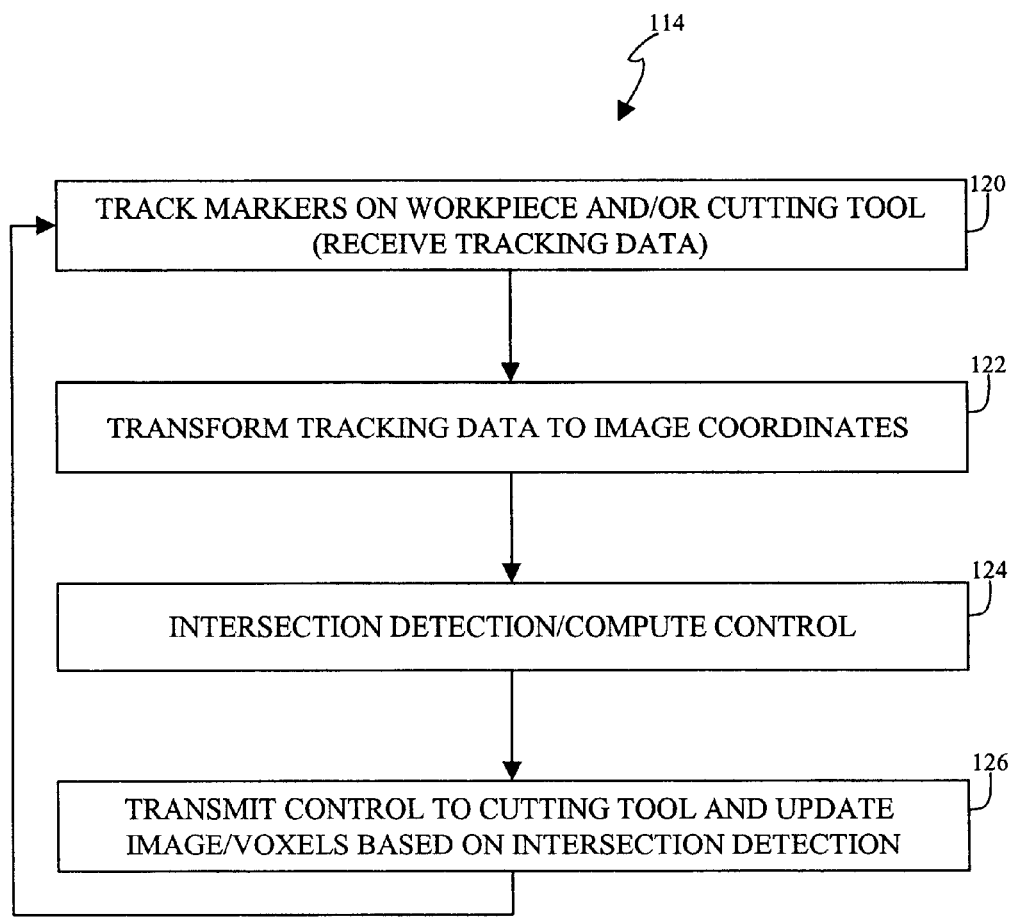
FIGS. 2A and 2B illustrate embodiments of the disclosed methods and systems.

FIG. 2A provides additional detail for one exemplary embodiment for the tracking and control method 114. As FIGS. 1 and 2 indicate, after image integration, probe calibration, and image registration, markers or other tracking scheme can be used to track the workpiece and the cutting tool 120. In an embodiment, the workpiece and the cutting tool can be tracked 120 in x, y, and z dimensions, and in three angles of yaw, pitch, and roll. As provided previously herein, in one system, the OPTOTRAK system can be used to track LEDs or other markers placed on the workpiece and/or cutting tool. In some embodiments, inertial data from, for examples, gyroscopes and/or accelerometers may be available to provide tracking data. The tracking data can be transformed to image coordinates 122 and intersection and/or collision detection can be performed or otherwise computed to provide a control for the cutting tool 124. Accordingly, based on the collision detection, the image/voxels can be updated and the cutting tool control data 126 can be transmitted to the cutting tool. In some embodiments, the control signal can be provided to a controller for the cutting element of the cutting tool. A method 114 according to FIG. 2A (and/or FIGS. 1 and/or 2B) can continue until, for example, the cutting tool is manually disabled and/or other condition occurs to terminate the method.

Figure 2B:
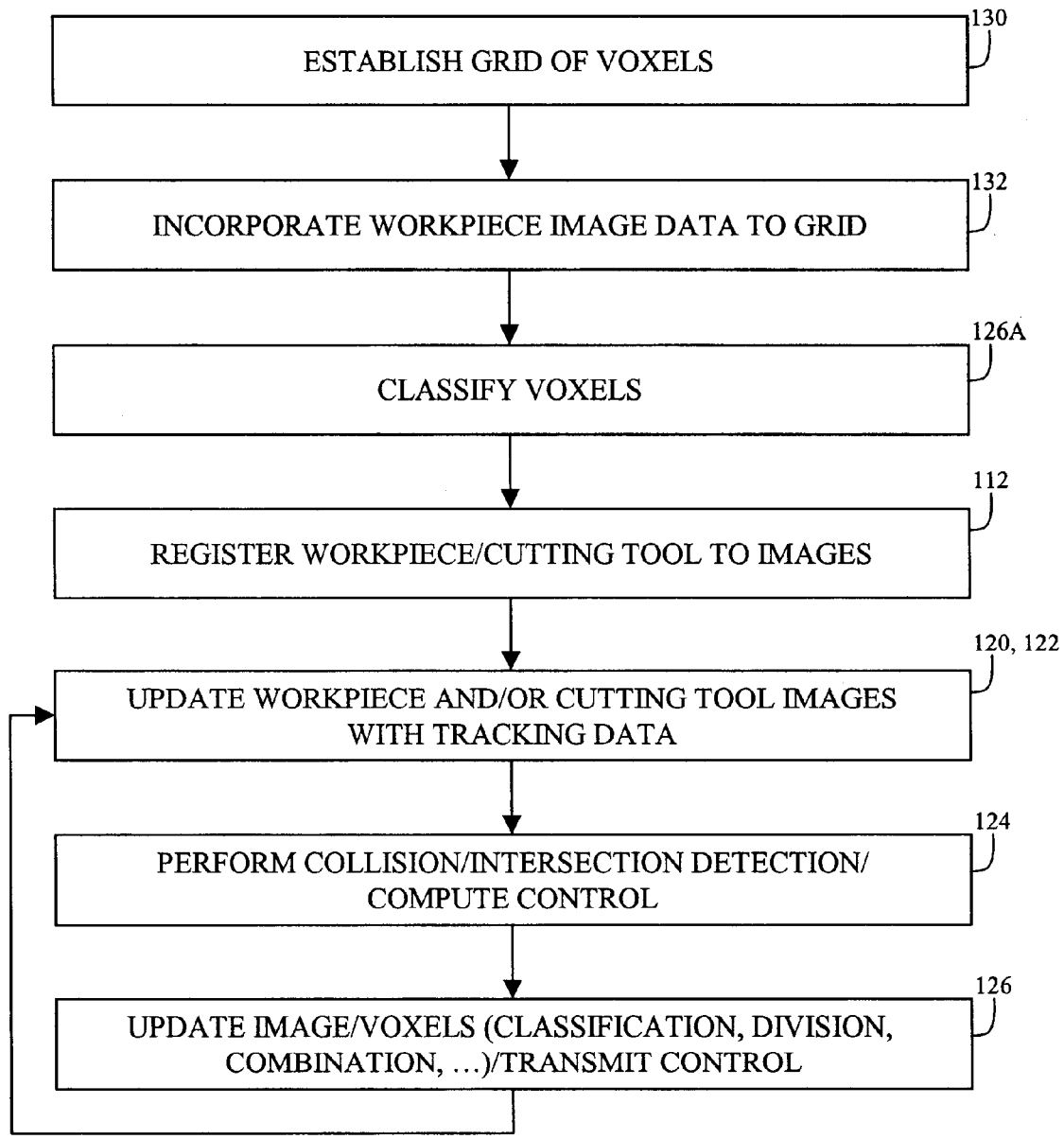

For one embodiment of the methods and systems that employs voxels to represent the workpiece and/or the cutting tool, updating the image 126 as provided according to FIGS. 1, 2A, and 2B can include classifying voxels. Those of ordinary skill will accordingly understand that several different voxel classification schemes can exist, including but not limited to those provided herein. Such schemes may, for example, be selected or otherwise chosen based on features of an embodiment and may be selected according to user selection and/or input. Such classification schemes may also be considered relative to integration with collision detection schemes and/or modules, desired precision levels, cutting tool control parameters and/or features, and other factors.

For example, in one embodiment, voxels corresponding to the integrated workpiece image can be categorized as "waste", "target", or "mixture". Voxels can also be characterized as "empty". An "empty" voxel could be designated where there is no workpiece material. This could occur, for example, where no material was ever present. A voxel previously designated other than "empty" could be redesignated "empty" once the material in the region corresponding to the voxel was removed during shaping. In an embodiment, where voxels can be used to represent the cutting tool, and in one embodiment, may be designated and/or classified as "tool", "free", or "mixture."

In one embodiment, voxel updating 126 can include an octree methodology that can be used to subdivide and/or otherwise manage "mixture" voxels (e.g., cutting tool and/or workpiece) until such voxels are classified as something other than "mixture." Accordingly, one voxel can be subdivided into eight sub-voxels, where the sub-voxels may be the same size.

In an embodiment, voxels can be used to designate the cutting element portion of the cutting tool, and may have classifications accordingly.

In some embodiments, the cutting tool image may not be voxellated but may be provided as an image with certain dimensions, where such dimensions may be known relative to the tracked positions on the cutting tool.

Those of ordinary skill will thus recognize that other "mixture" type voxels can be provided by the disclosed systems and methods. For example, a mixture voxel can be part-workpiece and part empty, or part-target and part-empty. Other variations of voxel classifications can be developed based on the embodiment, and accordingly, those of ordinary skill will recognize that the subdivision and recombining processes provided herein can be applied to other such types of mixture voxels until the mixture voxels are subdivided to a predetermined voxel resolution. In one embodiment, mixture voxels at the predetermined resolution can be classified based on the majority of the voxel.

Figure 3A:
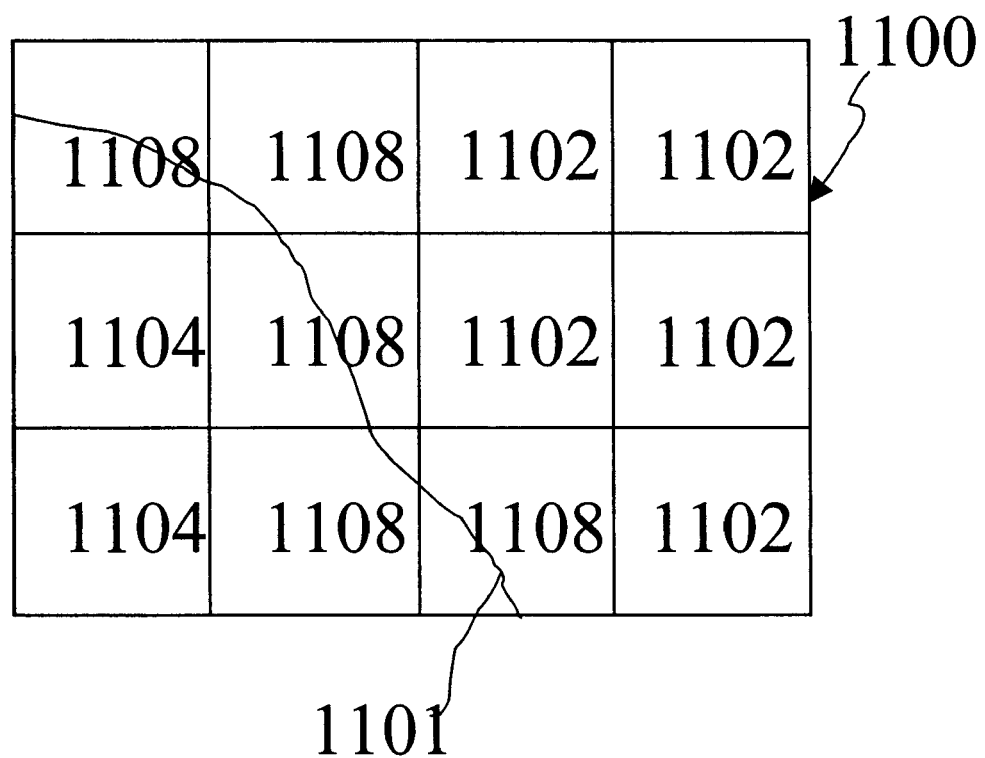
FIGS. 3A–3B provide schematic diagrams of embodiments of voxellation.

FIG. 3A depicts an exemplary embodiment of a voxellated image 1100 that includes an edge of a target where such edge boundary is shown as 1101. This example is depicted in two dimensions for clarity and simplicity of illustration, but the principle may be extended to three-dimensions. Voxels entirely within the boundary of the illustrated target shape can be classified and/or designated "target" voxels and are labeled by 1104, while voxels entirely outside the target shape can be classified or otherwise designated "waste" voxels and are labeled as 1102. As FIG. 3A indicates, voxels neither completely within the boundary of the illustrated target nor completely outside the boundary of the illustrated target can be classified and/or designated "mixture" voxels and are labeled 1108.

Figure 3B:
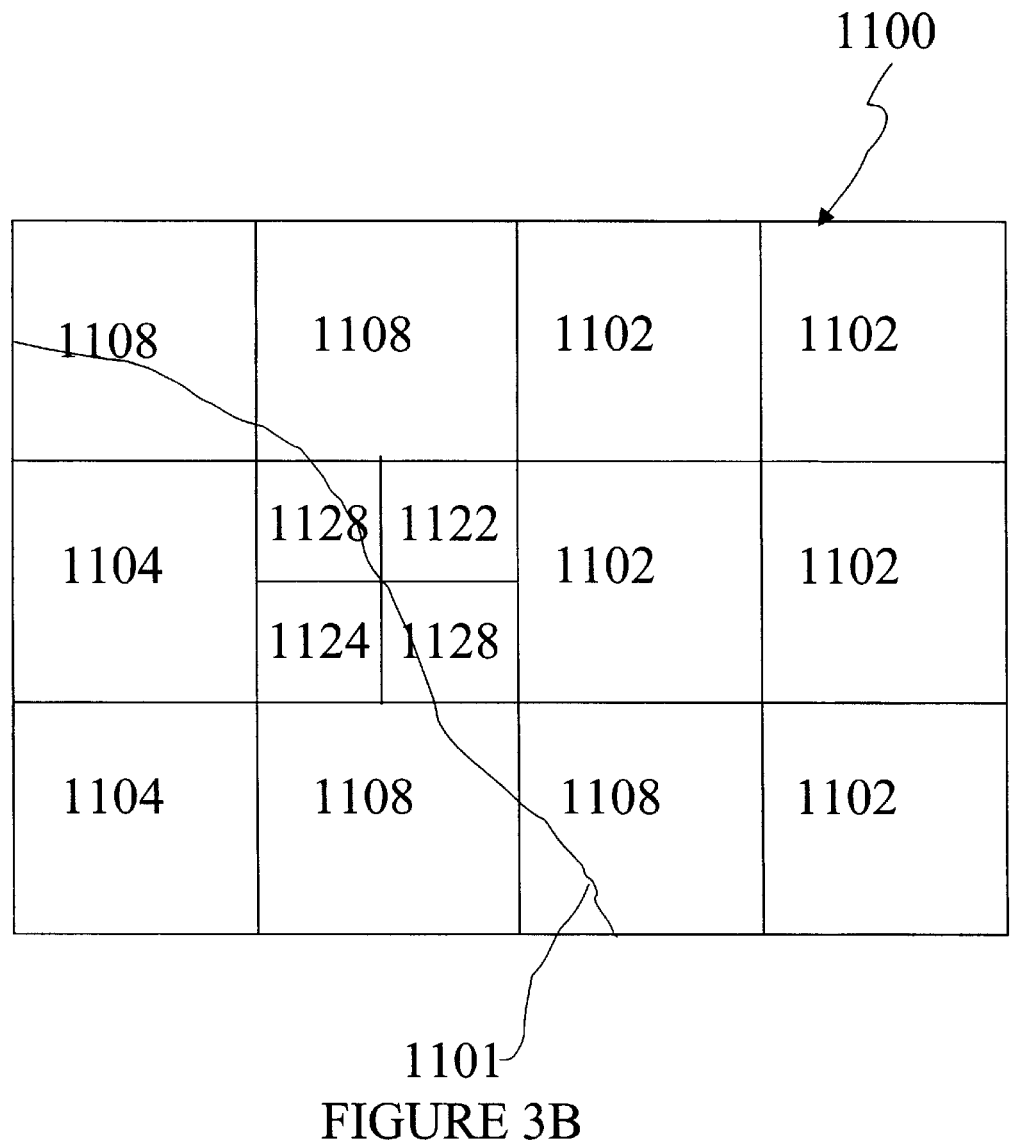

FIG. 3B presents another illustration of the image voxels of FIG. 3A, where one of the mixture voxels of FIG. 3A is further subdivided, where as provided herein, such subdivision can be managed using an octree methodology, although such three-dimensional method is not illustrated herein. As FIG. 3A indicates, the FIG. 3B mixture voxel can be represented as sub-voxels having a smaller dimension than the original voxels. The sub-voxels may be classified in like manner as the target, waste, and mixture, for example, per the voxels of FIG. 3A. Accordingly, one of ordinary skill will recognize that FIG. 3B depicts "waste" sub-voxels 1122, "target" sub-voxels 1124, and "mixture" sub-voxels 1128. A "mixture" sub-voxel may thus be further subdivided to yield sub-sub-voxels of still smaller size. Such classification and subdivision may continue in like manner until, for example, a desired resolution is achieved and/or until no "mixture" voxels remain (i.e., voxels are designated either "target" or "waste").

Additionally and/or optionally to the subdivision of "mixture" voxels, a recombination or merging of non-mixture (e.g., "waste" and "target") voxels based on an octree and/or other management scheme can be performed with commonly designated neighbors to define larger-dimensioned voxels that encompass like-classified voxels. One of ordinary skill in the art will recognize that a process of forming progressively larger "target" and "waste" voxels can simplify an image representation of the integrated workpiece image, thereby reducing the storage space and/or computation time associated with storing and/or manipulating the integrated workpiece image.

In some embodiments, additional categorizations for voxels may be provided. In one embodiment, voxels can be categorized as "near-waste" or "near-target" to indicate voxels in a given proximity of "waste" or "target" voxels, respectively. In some embodiments, a "mixture" voxel can include mixtures of target and waste, mixtures of target and near-target, mixtures of waste and near-waste, mixtures of target and empty, mixtures of waste and empty, mixtures of near-waste and empty, mixtures of near-target and empty, and mixtures of more than two designations. In an embodiment, a "mixture" voxel may be subdivided into sub-voxels of different designations. For example, a mixture of waste and target could be subdivided into voxels of "near-waste" and/or "near-target" in place of or in addition to sub-voxels designated "waste" and/or "target".

Figure 4A:
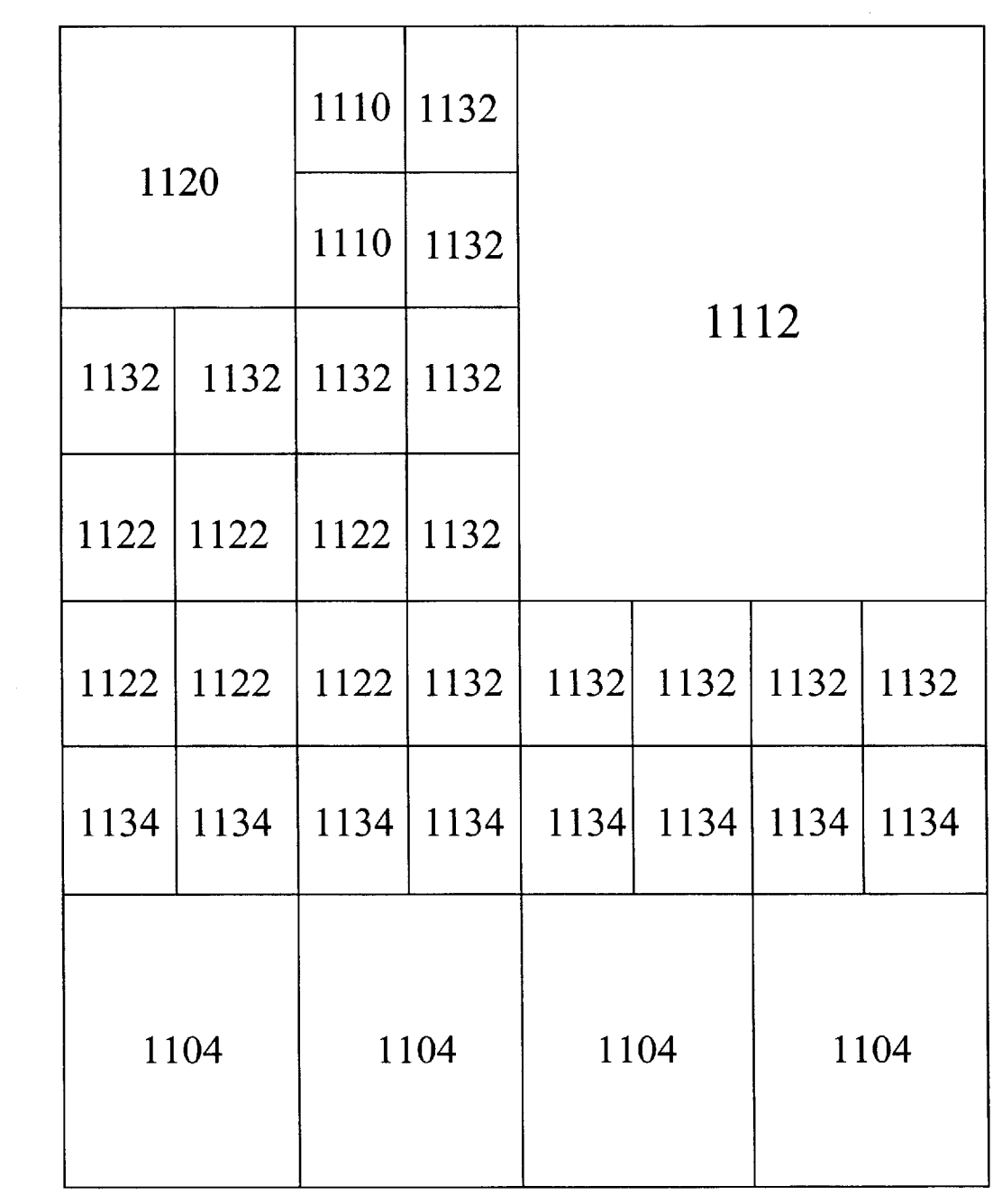

FIGS. 4A–4C depict three figures that illustrate voxel classification, voxel reclassification, voxel subdivision, and voxel recombination one embodiment. FIG. 4A depicts one embodiment where the image 1100 includes, among others, "target" voxels 1104, an "empty" voxel 1120, and a "waste" voxel 1112. These voxels are of varying size due to voxel subdivision and/or recombination. As shown, other classifications can be used, such as near-target sub-voxels 1134, and "near-waste" sub-voxels 1132. Other "empty" sub-voxels 1110 can be a results of subdivisions of other "mixture" voxels (not shown) that included at least part empty classification. Also, other sized "waste" sub-voxels 1122 also can be derived from "mixture" voxels (not shown) that included at least some waste. As will be readily apparent, voxels of "near-waste" and "near-target" and other designations can be subdivided or merged as described above for "waste" and "target" voxels. In the illustrated embodiment of FIG. 4A, no mixture voxels are shown for simplicity of illustration.

FIG. 4B depicts another embodiment where material in a space corresponding to a voxel can be considered removed if a cutting tool is determined to occupy or to have previously occupied the space. In FIG. 4B, the material in the space corresponding to near-waste sub-voxel 1132 of FIG. 4A has been removed, the voxel reclassified as "empty", and the voxel merged with its neighbors to create a new "empty" voxel 1120'. Waste voxel 1112 of FIG. 4A is subdivided in FIG. 4B to create, among others, new waste voxel 1102', new waste sub-voxel 1122", and new near-waste sub-voxel 1132".

FIG. 4C depicts additional material being removed by the cutting element based on FIG. 4B. As FIG. 4C indicates, voxels and/or sub-voxels can be reclassified as "empty" and merged with "empty" neighbors to form a merged empty voxel 1130. At least some of the material corresponding to waste sub-voxels 1122 of FIG. 4B have also been removed and the sub-voxels reclassified as empty sub-voxel 1110'. In the illustrated embodiment, empty sub-voxel 1110' is adjacent to near-waste sub-voxel 1134. In an embodiment, the adjacency of empty voxels, empty sub-voxels, or other empty voxel subdivisions to near-target or target voxels, sub-voxels, or other voxel subdivisions can cause a "stop" command to be sent to the shaping or cutting tool to prevent invasion of target or near-target voxels. In an embodiment, near-target voxels, sub-voxels, or other voxel subdivisions can be subdivided into, e.g., target, near target, waste, near waste, and/or empty subdivisions to facilitate cutting or shaping of increasing precision. One of ordinary skill can thus understand that the disclosed methods and systems can facilitate a classification of voxels (e.g., near-target) that can be enlisted to enhance a collision detection and/or interference detection determination.

One of ordinary skill in the art will also thus recognize that in embodiments that voxellate the cutting tool, the cutting tool voxels can also be classified as provided previously herein, where such "mixture" voxels can be further subdivided and/or combined as provided herein relative to the integrated workpiece image voxels.

Accordingly, referring back to FIGS. 1 and 2, a control computation 126 for computing a control command(s) for the cutting tool can include performing collision detection between the (integrated) workpiece image and the cutting tool image. Accordingly, voxels can be classified 124 based on collision detection, and accordingly, voxel subdivision and/or recombination can occur as desired (e.g., eliminate mixture voxels, recombine) to update the image(s). Those of ordinary skill will recognize that not all parts of the image may require re-voxellation with an iteration of a method or process according to FIGS. 1, 2A, and/or 2B.

Accordingly, when the cutting tool and/or element is about to or does impinge or otherwise invade a voxel categorized as target, a control signal may be transmitted to the cutting element controller to cause the cutting element to retract and/or be inactivated. Similarly, as the cutting element is moved to areas that can be associated with a voxel categorized as waste, a control signal can be transmitted to the cutting element controller to allow operation of the cutting element.

Those of ordinary skill in the art will recognize that the methods and systems disclosed herein can include a method and system of collision detection through the use of voxels and the octree. Such collision or interference detection can allow the processor to compare the relative positions of the cutter and workpiece to the integrated workpiece image/classified voxels, to compute a control signal that prevents or otherwise reduce the probability of invasion of the cutting element to the target shape. Accordingly, such control can be based on the relative and/or predicted positions of the workpiece to the cutting element/tool, a measured and/or predicted velocity of the cutting element/tool and/or workpiece, angles of rotation, voxel sizes, voxel classifications, sampling rate, and other data.

FIG. 2B provides another illustrative example of the disclosed systems and methods that provides additional detail for various elements of the methods and systems disclosed relative to FIGS. 1, 2A and as otherwise provided herein. In an embodiment according to FIG. 2B, a grid of voxels can be provided 130, where such grid can be of a predetermined number of voxels, and can allow a user or another to specify a dimension for the grid voxels via a user interface or another input data means. In one embodiment, the grid can correspond to a surgical field in which a surgical procedure is being performed. For example, a processor can be configured to provide a grid of voxels 130 of size 100×100×100 voxels, although such illustrative size is not a limitation, and other sizes can be used, where such sizes can include different numbers of voxels in the three different dimensions. A user may indicate that a voxel side can be, for example, 1 inch, 1 millimeter, or another size, with such sizes being merely illustrative. Accordingly, an integrated workpiece/target image can be sampled and/or incorporated into the grid 132. Based on the integrated workpiece's position within the grid, the size of the workpiece, and the size of the voxels, grid voxels can be classified as "good", "waste", or "empty" 126A, where such designations are illustrative examples of voxel classifications. Calibration can be performed as provided herein, as well as registration 112, and based on the calibration and registration of the workpiece, the workpiece and grid can be associated with at least a position in 3-D space. Similarly, the cutting tool can be tracked in 3D space. As provided herein relative to at least FIG. 1, tracking data can be received, where such tracking data can be associated with the workpiece and/or the cutting element 120, 122. Based on tracking data that can be transformed to the image coordinate system, 120, 122, collision detection can be performed and a control command computed 124. The respective workpiece and/or cutting tool images and associated voxels can thereafter be updated 126 as provided herein, to reflect relative positions in 3-D space. Such updating can include one or more iterations of subdivision, recombination, and/or (re)classification. As provided herein, voxel subdivision can be based on an octree scheme, although other schemes may be used. Those of ordinary skill will recognize that coordinate translations and/or transformations of the tracking data can be performed as needed per the embodiment.

Collision detection and/or interference detection can be performed 124, where such detection can be based on computed distances between the cutting tool (and/or cutting element) and the waste/good elements of the workpiece. For example, in one embodiment, if the 3D position of the cutting element is not within a specified distance of the workpiece, it may be understood that the cutting tool is sufficiently distant from the workpiece such that it may be desirable to disable the cutting tool with a corresponding control command.

Based on respective sizes of voxels, for example, a distance can be computed between the cutting tool/element and the workpiece.

In one embodiment, interference detection can be performed in addition to or alternative to a distance computation. For example, in one embodiment, to determine whether the cutting tool and/or element may intersect with "good" voxels of the workpiece, the cutting tool image can be artificially increased and voxellated based on an increased size. Such increased size can be constant throughout in some embodiments, while in other embodiments, the cutting tool and/or element size can be artificially increased based on an iteration of the systems and methods of FIGS. 1, 2A, and/or 2B. For example, the artificial increase in size of the cutting tool/element can be based on a voxel size, a tracking uncertainty, one or more tracking parameters (e.g., velocity, acceleration, angle), one or more predicted tracking parameters (e.g., position, angle, etc.), a desired cutting precision, and/or other factors. In an embodiment that uses an artificially increased cutting tool, a collision determination can provide a binary output (e.g., collision, non-collision) to provide a corresponding control.

In one embodiment, a control may be provided to the cutting tool/element based on the distance and a user-designated cutting precision. For example, a user may designate or otherwise input relative precisions of cutting precision at different times. In an embodiment, cutting precision may be automatically computed based on voxel sizes in the vicinity of the cutting tool and the "good" voxels.

In some embodiments, to aid the user or operator of the cutting tool, classified voxels can be color coded. For example, waste voxels can be translucent and/or clear, while target (e.g., "good") voxels may be solid. Alternatively, target shape voxels can be transparent, while waste voxels can be solid to facilitate visualization of material to be removed. Other systems for classifying and/or designating voxels can be used. Similarly, other methods and system for providing collision detection can also be implemented without departing from the scope of the disclosed methods and systems. For example, collision detection can include a KD-tree, an AABB-tree, a bounding box technique, a closest-point calculation, a voxel-based bounding box, and other techniques.

In an embodiment, the control signal provided by the computer to the cutting tool/element can be an analog signal that can be received by a driver box, although in other embodiments, the signal may be digital. The driver box can thereafter transmit a signal to a motor or other component of the cutting tool/element, to provide cutting tool/element control. Furthermore, in some systems and methods, the cutting tool can include an ultrasonic motor that can transmit an encoder signal to allow the computer to track the motor characteristics (e.g., speed, rotation, etc.).

Illustrative image feedback systems that can provide guidance to a user of a cutting tool, where such feedback systems are described in U.S. Pat. Nos. 5,880,976 and 6,205,411, the contents of which are incorporated herein by reference.

In some embodiments, a robot can control the cutting tool and can be programmed to cut a predetermined shape from the workpiece. In other embodiments, manual control can be used to used to facilitate fine control of the cutting. Combinations of manual and robotic control can be used. The disclosed systems and methods can thus be utilized regardless of whether the cutting tool user is human or non-human.

As provided previously herein, multiple cutting elements can be used, wherein the different cutting elements can be characterized in the computer for proper tracking and registration (and voxellation). For example, one cutting element can include different types of attachments. A user can change the computer profile (e.g., image) of the cutting element based on the attachment. One attachment can be used to cut while another attachment may grind waste material. Additionally and optionally, the surface characteristics of the cutting element can be considered and provided to the computer for more accurate tracking and registration (and voxellation).

The cutting tool can be a freehand instrument, although in some embodiments, the cutting tool can be restricted in movement as is well known in some robotic applications.

Those of ordinary skill in the art will recognize that the tracker as provided herein can include a predictive tracker that can utilize, for example, a Kalman filter or other predictive or estimation module to control the cutting element by predicting position, at least, of the cutting tool/element in a next measurement interval. In a predictive tracking embodiment, the tracker/controller can predict position, velocity, and/or acceleration of the cutting tool/element, for example. In some embodiments, the tracker can vary the speed of the cutting element. The tracker can determine the position of the cutting tool/element based on a known prior position and on velocity and/or acceleration data. The tracker may also predict a future position of the cutting tool/element based on a known prior position and on velocity and/or acceleration data. Position prediction can help prevent or otherwise reduce the likelihood of invasion of target or near-target material by the cutting tool/element as future invasion can be predicted and a signal sent or interrupted to the cutting tool/element to alter its interaction with the workpiece, as described herein.

The tracking, control, registration, calibration, image generation and updating, voxellation, and other processes, provided herein as residing on a computer or other processor-controlled device, can be understood to be processes that can be implemented on one or more processors that can be one or more like or dissimilar devices that can be communicatively connected via wired or wireless communications. Additionally and optionally, the processes can be implemented in hardware or software, and combinations thereof.

Figure 5:
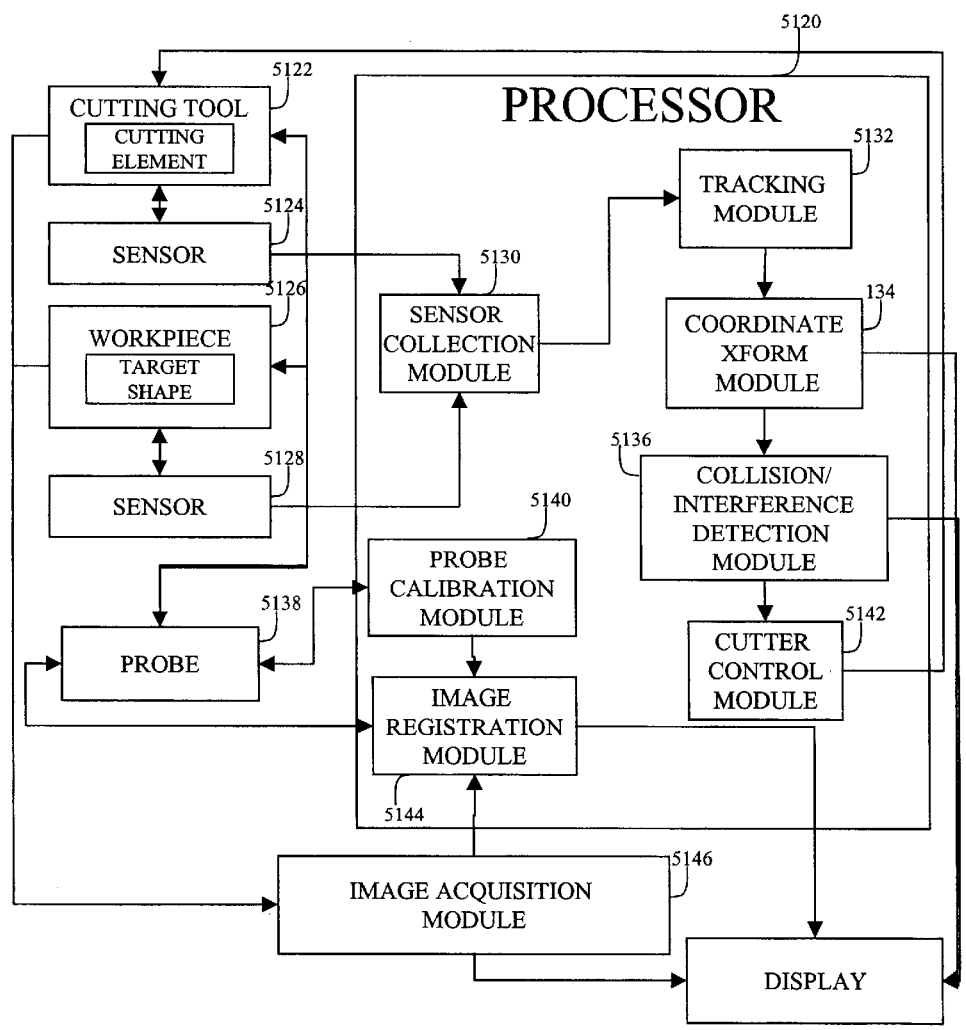
FIG. 5 is an architectural block diagram of one embodiment.

Accordingly, FIG. 5 provides an illustrative system that provides one embodiment where the components of the system can be viewed as modules that reside on or otherwise can be associated with a processor 5120, although as provided herein, the modules are merely illustrative, as are their representative communicative connections and relations. In an embodiment, the modules can reside on individual processors.

As FIG. 5 indicates, the probe 5138 can communicate with a probe calibration module 5140. Images of the cutting tool/element 5122 and the workpiece 5126 can be provided to an image acquisition module 5146 or other interface means. As provided previously herein, data provided by touching the surface of the cutting tool/element 5122 and workpiece 5126 can be provided with the image data from the image acquisition module 5144, respectively, to an image registration module 5144 that can associate the coordinates of the cutting tool/element 5122 and the workpiece 5126 to their respective image data 5146. As provided herein, the image acquisition module can include a scanner, a digital image, X-ray, CT scan, etc., and the image acquisition module can be a system integrated with the processor 5120, or distinct from the processor 5120 such that the image data can be transferred to the processor 5120.

A sensor collection module 5130 can collect data from the sensors that can include infrared data, ultrasound data, or other data based on sensors 5124, 5128 associated with the cutting tool 5122 and workpiece 5128. The sensors 5124, 5128 can be the same or distinct, can be affixed to the cutting tool 5122 and/or workpiece 5126, and/or may be located separately from the cutting tool 5122 and workpiece 5126. The sensor collection module 5130 can thus include a receiver and/or detector to receive signals or other data from the sensors 5124, 5128, and signal conditioning modules including filters, amplifiers, and/or analog-to-digital converters, for example. In one embodiment provided herein, the sensor collection module includes an optical device to sense LEDs.

A sensor tracking module 5132 can receive the signal data from the sensor collection module 5130 and process the data to provide measurements that can include coordinates of the cutting tool 5122 and workpiece 5126 in x, y, z coordinates, and angles of yaw, pitch, and roll, although other coordinates can be used, and fewer or more degrees of freedom, or combinations thereof, can be used. For one embodiment provided herein that tracks marker positions (e.g., sensors) on the cutting tool 5122 and workpiece 5126, the second x, y, z and roll, pitch, and yaw can be related to the marker. Such positions and angles can thus be transformed 5134 to a coordinate system compatible with the coordinate system of the images that also include the positions of the markers. Based on the computed positions of the two markers and the known respective geometries of the cutting tool 5122 and workpiece 5126, a collision detection module 5136 can compute the intersection of the cutting tool 5122 and workpiece 5126 to determine whether the cutting tool 5122 is invading target voxels of the workpiece 5126. Accordingly, the collision detection module can include a voxellation module to update the voxellated workpiece based on the cutting tool position. Based on the collision detection module determination, a command or other measurement can be provided to a cutter control module 5142 that can generate or otherwise provide a signal for delivery to the cutting tool and/or cutting element 5122. As provided herein, such command can include data to stop the cutting element, to retract the cutting element, or to change the speed of the cutting element, for example. The cutter control module 5142 can thus include or otherwise interface to an antenna, output port, bus, relay, switch, or other means to transport data to the cutting tool/element 5122.

One of ordinary skill in the art will recognize that the methods and systems disclosed herein can utilize wired or wireless communications, or a combination thereof, as desired.

Figure 6:
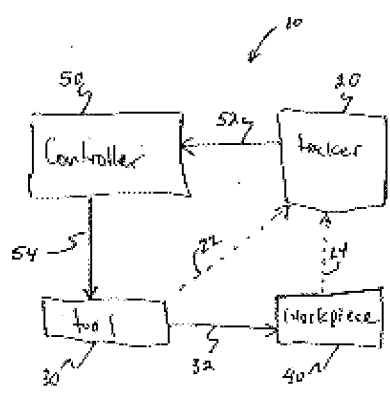
FIGS. 6 and 7 depict embodiments of cutting systems.

FIG. 6 depicts another exemplary embodiment of a cutting system 10. A tracker 20 can receive signals 22, 24, from a tool 30 and a workpiece 40, respectively. The tool 30 can interact 32 with the workpiece 40. The interaction 32 can include cutting the workpiece 40 or not cutting the workpiece 40. The interaction 32 can also include cutting the workpiece 40 at a diminished rate. A controller 50 can receive a signal 52 from the tracker that can include position information for at least one of the tool 30 and the workpiece 40. The controller 50 can include a representation of a target shape (not shown) of the workpiece 40. Based, for example, at least in part on the signal 52 from the tracker 20, the controller 50 can determine whether the tool 30 may be invading (e.g., based on tracking information, predictive estimates, etc.) the target shape. If the tool 30 may invade the target shape, the controller 50 can transmit a signal 54, for example, to the tool 30, where transmitting a signal, which can include interrupting a signal, or otherwise transmitting no signal. The transmitting of such a signal 54 may cause the tool 30 to change its interaction 32 with the workpiece 40.

Figure 7:
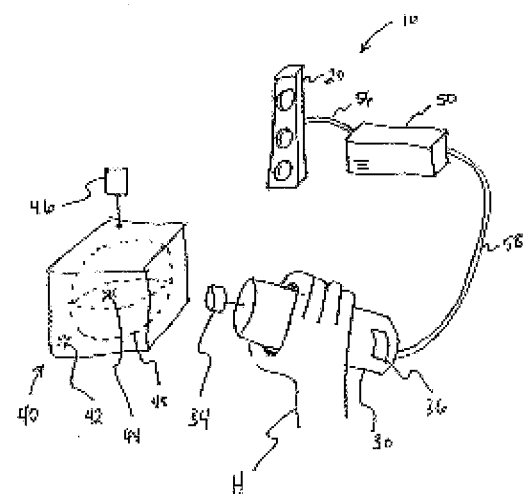

FIG. 7 also depicts an embodiment of a cutting system 10. A user can hold the tool 30 by hand H. The illustrated tool 30 includes a cutting element 34 that can cut material from the workpiece 40 that includes waste material 42 and non-waste material 44 that is otherwise part of a target shape 48. The shapes of the workpiece 40, the waste material 42, the non-waste material 44, the target shape 48, and other elements as depicted in FIG. 2 are only exemplary. The target shape 48 can be defined by a plurality of points or surfaces. As provided herein, before cutting begins, the waste material 42 and the non-waste material 44 may be integrated to form the whole of the workpiece 40, and the waste and target shapes may include the same substance and may be indistinguishable by sight or by other properties. The target shape 48 can be represented in the controller 50 as, for example, a set of points within the workpiece 40 that distinguish waste material 42 from non-waste material 44. The user can plan the target shape 48 and instruct the controller 50 as to its nature.

As provided previously herein, the tracker 20 and markers 36, 46 can be, for example, as described in U.S. Pat. Nos. 5,828,770; 5,923,417; 6,061,644; and 6,288,785, the contents of which are incorporated herein by reference. Other tracking systems may be employed, such as radio-frequency (RF) tracking, ultrasound tracking, electromagnetic tracking, including "Flock of Birds" tracking, as those described in U.S. Pat. Nos. 4,849,692; 5,600,330; 5,742,394; 5,744,953; 5,767,669; and 6,188,355, the contents of which are incorporated herein by reference. Connections 56, 58, may be provided between the tracker 20 and controller 50, and between the controller 50 and the tool 30, respectively. The connections may include an electrical connection, a fluid connection, or a light connection such as an optical fiber. The connections 56, 58, may also include RF or other wireless connections that may not require a physical connection, as is depicted by way of example in FIG. 2.

The user may shape the workpiece 40 by applying the cutting element 34 of the cutting tool 30 to the workpiece 40. Waste material 42 can be removed if the cutting element 34 is in an orientation or condition for cutting. An orientation or condition for cutting can depend on what type of cutting element 34 is employed. For example, if the cutting element 34 is a rotating blade, then a cutting condition can be rotation of the blade. In this example, waste material 42 can be removed if the blade is rotating. Cutting can be modulated by slowing or stopping the blade. In another example, the cutting element 34 can be a retractable blade. In this example, a cutting condition can be rotation of the retractable blade, and another cutting condition can be extension of the retractable blade. In yet another example, the cutting element 34 can include a jet of a material such as water, or a particulate such as sand. In this example, a cutting condition can be delivery of the material through the jet. Cutting can be modulated by slowing or stopping the delivery of material by at least partially closing a valve, stopping or slowing a pump, diverting the material. In another example, the cutting element 34 can include a lithotriptor. A lithotriptor can, for example, disrupt at least a part of the workpiece 40 by delivering a shock wave to the workpiece 40. The cutting element 34 can include an ultrasonic generator to deliver the shock wave. Other embodiments of cutting element 34 may include heater, chipper, cautery, electrocautery, abraiser (such as sandpaper), suction, screw, scissors, and scalpel, and other devices known in the art for eliminating, excising, wearing, or cutting material.

Figure 8:
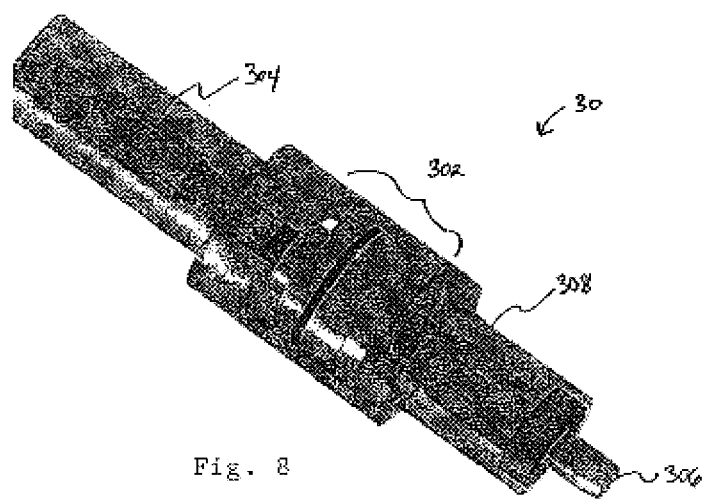
FIGS. 8 depicts an embodiment of a handheld cutting tool.

FIG. 8 depicts an exemplary embodiment of the cutting tool 30. The tool 30 may have a clutch 302 that can selectively couple a drive shaft 304 to a cutting element (not shown), the cutting element disposable on a collet 306. The tool 30 may have a casing 308, illustrated in FIG. 8 as translucent to show detail.

Figure 9A:
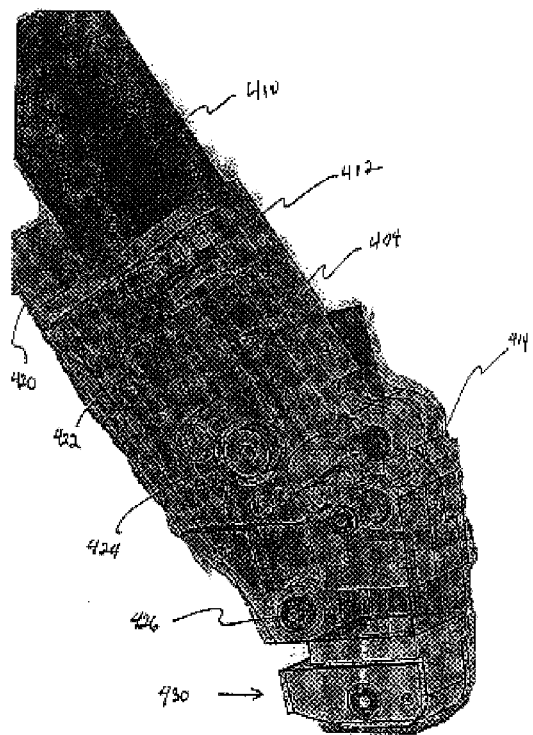
FIGS. 9A and 9B depict an embodiment of a cutting tool with a retractable head.
Figure 9B:
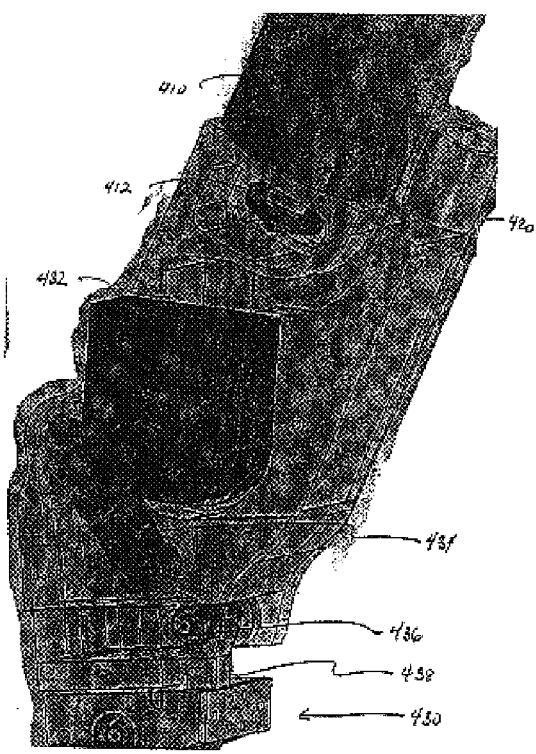

FIGS. 9A and 9B depict front and back views, respectively, of an exemplary embodiment of a tool 30 including a retractable blade. The tool 30 can have a power system. The power system can have a power motor 410 which can provide power and couple to a drive shaft 404 through a set of gears 412. The drive shaft 404 can couple to a drive pulley (not shown) through a set of bevel gears 414. The drive pulley can couple to a head drive pulley in the cutter head 430 with a timing belt, as described below. A tensioner 434 can absorb slack in the timing belt when the blade is repositioned. The tool 30 may have a suction port 420 in communication with a suction channel 422 through which waste material and other debris may be removed from a work area.

Retraction and extension of the retractable blade may be accomplished with an adjustment system. An adjustment motor 432 may be in communication with a controller as described above. In an embodiment, the adjustment motor 423 can be an ultrasonic motor. Ultrasonic motors may be preferred due to fast response time. The adjustment motor 432 may be connected to a top adjustment pulley 424, which can drive a timing belt (not shown) that may couple to a lower adjustment pulley 426. A cam 436 can be connected to the lower adjustment pulley 426. The cam 436 can convert the rotational motion of the lower adjustment pulley 426 into linear motion of the retractable blade by pushing on an arm 438 of the cutter head 430. In response to a signal from a controller, the adjustment motor 432 can drive the adjustment system to effect retraction or extension of the blade.

In an embodiment, an ultrasonic motor can be driven by a high frequency signal which may be generated by a driver box and can be tuned to the ultrasonic motor. In an embodiment, a tool can return a digital raw quadrature signal.

Figure 10A:
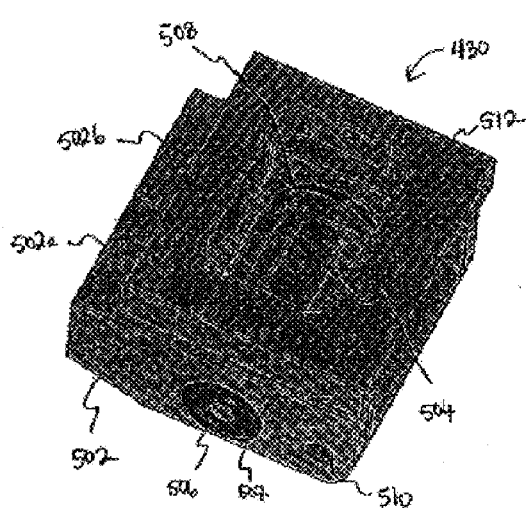
FIGS. 10A and 10B illustrate an exemplary cutting head.
Figure 10B:
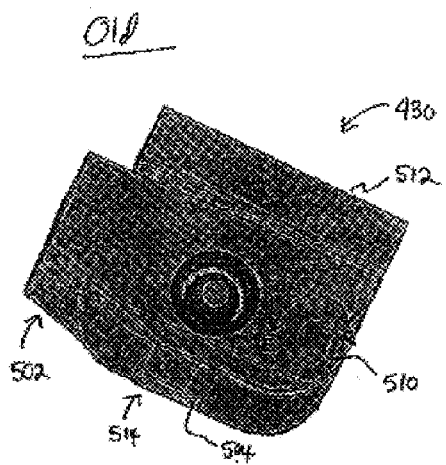

FIGS. 10A and 10B depict an exemplary embodiment of a cutter head 430. The cutter head 430 may be removably attachable to the tool 30. The cutter head 430 can include a blade carrier 502. The blade carrier 502 may be formed of two components or halves, 502a, 502b. Splitting the blade carrier 502 thus may facilitate assembly of the blade carrier 502. A blade 504 may be disposed in the blade carrier 502 and mounted on a blade axle 506. The blade 504 and blade axle 506 may be driven by a drive pulley 508, as described previously. The blade axle 506 can be supported by a bearing 507. The blade carrier 502 may rotate with respect to a cutter body 512 at a hinge pin 510. The cutter body 512 can have an aperture 514 through which the blade 504 may protrude when the blade carrier 502 is rotated with respect to the carrier body 512 in direction E. The blade 504 may retract from the aperture 514 when the blade carrier 502 is rotated with respect to the carrier body 512 in direction R.

Figure 11A:
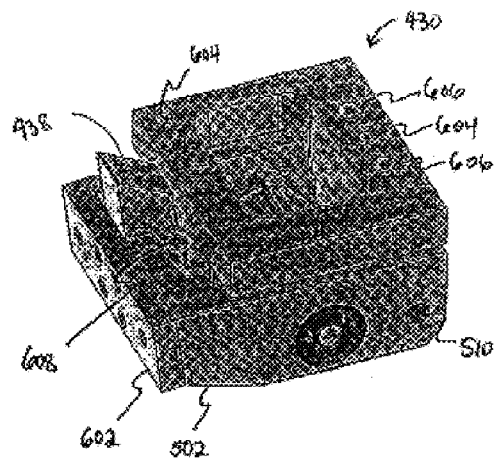
FIGS. 11A and 11B also illustrate an exemplary cutting head.
Figure 11B:
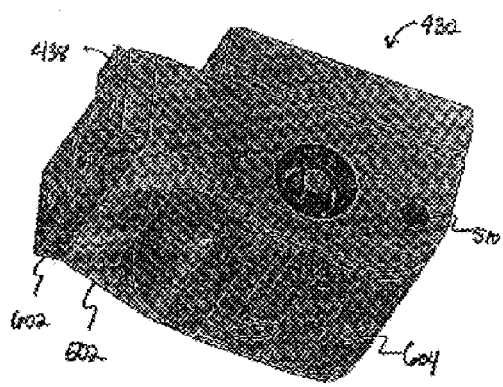

FIGS. 11A and 11B show another exemplary embodiment of the cutter head 430. The cutter head 430 may further include the arm 438, which can receive the cam (not shown) and displace the blade carrier 502 at the hinge pin 510. A plate 602 can join the components of the blade carrier 502. A spring 608 may be attached to the blade carrier 502 to oppose the push of the cam on the arm 438 and help tend to keep the blade carrier 502 in the retracted position. Alternatively, the spring can be attached to the tool and couple to the blade carrier 502. The cutter head 430 may be attached to the tool by screws that can thread into screw holes 604. The blade carrier 502 can also have an alignment system to help ensure a precise fit between the cam, the arm 438, and the blade carrier 502. In the depicted exemplary embodiment, the alignment system includes dowel holes 606.

Figure 12:
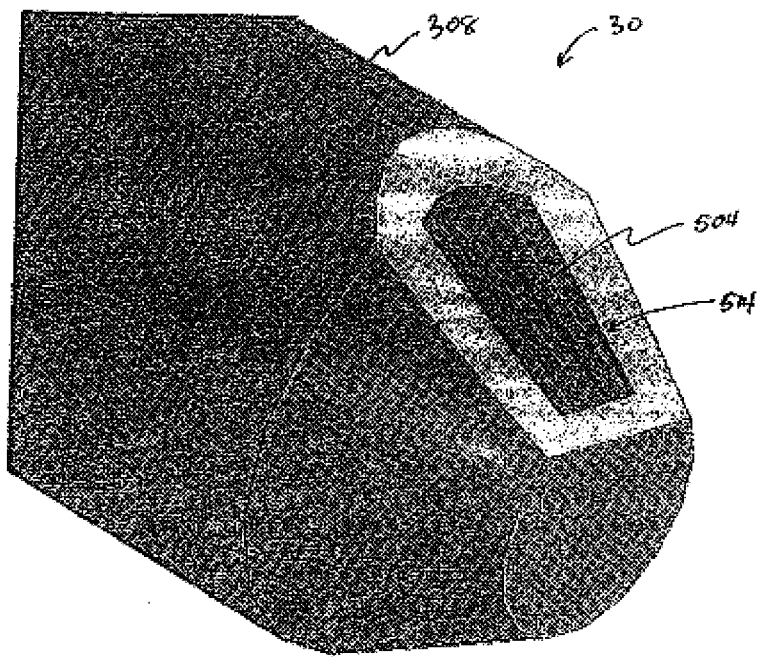
FIG. 12 provides a cutting tool for endoscopic use.

FIG. 12 depicts an external view of another exemplary embodiment of a tool 30 that can be adapted for endoscopic deployment and use. The blade 504 may be extended or retracted with respect to an aperture 514. The tool 30 may include a casing 308. The casing may be formed of plastic or metal. The casing 308 may have a lubricious coating (not shown) to facilitate displacement of the tool 30 through a cannula. Examples of lubricious coatings include but are not limited to polyethylene, silicone, and hydrophilic substances.

Figure 13:
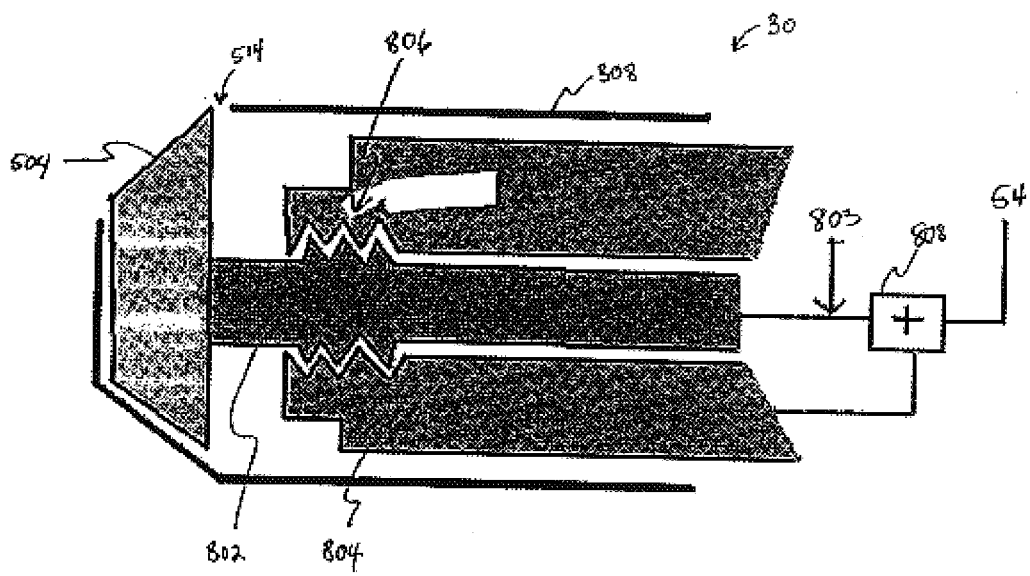
FIG. 13 shows a cross-section of the FIG. 12 tool.

FIG. 13 depicts a cross-section of the tool 30 shown in FIG. 12. The blade 504 may advance or retract through an aperture 514 in the casing 308. The position of the blade 504 may be controlled by an inner shaft 802 and an outer shaft 804. The inner shaft 802 and the outer shaft 804 may be coaxial. The inner shaft 802 can couple to the blade 504 and cause the blade 504 to rotate when the inner shaft 802 rotates under drive power 803. The inner shaft 802 can couple to the outer shaft 804 by a series of threads 806. If the inner shaft 802 and the outer shaft 804 rotate at the same speed, then the blade 504 will neither advance nor retract. However, if different speeds are applied to the inner shaft 802 and the outer shaft 804 by a differential 808, then the blade 504 can be repositioned. For example, if the inner shaft 802 is given a greater speed than outer shaft 804, then the blade 502 can advance. Conversely, if the inner shaft 802 is given a lesser speed than outer shaft 804, then the blade 502 can retract. The differential 808 may set speeds of the inner shaft 802 and the outer shaft 804 in response to a signal 54 from a controller (not shown), as described above.

Those or ordinary skill in the art will recognize that the methods and systems disclosed herein have wide applicability to surgical and non-surgical techniques. For example, the disclosed methods and systems can be applied to embodiments and/or applications that may employ stereo lithography, fused deposition machine (FDM), architecture, sculpting, and other areas.

The disclosed methods and systems thus include methods and systems to track a workpiece and a cutting tool, transform the tracked coordinates to the image coordinates, update the images accordingly based on the workpiece and/or cutting tool characteristics (i.e., cutting element size, dimensions, physical characteristics, etc.), and compute a control signal for transmission to the cutting tool.

The methods and systems described herein are not limited to a particular hardware or software configuration, and may find applicability in many computing or processing environments. The methods and systems can be implemented in hardware or software, or a combination of hardware and software. The methods and systems can be implemented in one or more computer programs, where a computer program can be understood to include one or more processor executable instructions. The computer program(s) can execute on one or more programmable processors, and can be stored on one or more storage medium readable by the processor (including volatile and non-volatile memory and/or storage elements), one or more input devices, and/or one or more output devices. The processor thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processor as provided herein, where such aforementioned examples are not exhaustive, and are for illustration and not limitation.

The computer program(s) is preferably implemented using one or more high level procedural or object-oriented programming languages to communicate with a computer system; however, the program(s) can be implemented in assembly or machine language, if desired. The language can be compiled or interpreted.

The processor(s) can thus be embedded in one or more devices that can be operated independently or together in a networked environment, where the network can include, for example, a Local Area Network (LAN), wide area network (WAN), and/or can include an intranet and/or the internet and/or another network. The network(s) can be wired or wireless or a combination thereof and can use one or more communications protocols to facilitate communications between the different processors. The processors can be configured for distributed processing and can utilize, in some embodiments, a client-server model as needed. Accordingly, the methods and systems can utilize multiple processors and/or processor devices, and the processor instructions can be divided amongst such single or multiple processor/devices.

The device(s) or computer systems that integrate with the processor(s) can include, for example, a personal computer (s), workstation (e.g., Sun, HP), personal digital assistant (PDA), handheld device such as cellular telephone, or another device capable of being integrated with a processor (s) that can operate as provided herein. Accordingly, the devices provided herein are not exhaustive and are provided for illustration and not limitation.

Many additional changes in the details, materials, and arrangement of parts, herein described and illustrated, can be made by those skilled in the art. Accordingly, it will be understood that the following claims are not to be limited to the embodiments disclosed herein, can include practices otherwise than specifically described, and are to be interpreted as broadly as allowed under the law.

What is claimed is:

1. A system, comprising:
   a cutting tool;
   a workpiece that includes a target shape;
   a tracker to provide tracking data associated with the cutting tool and the workpiece, where the tracker includes at least one of: at least one first marker associated with the workpiece, and at least one second marker associated with the cutting tool; and
   a controller to control the cutting tool based on the tracking data associated with the cutting tool and the tracking data associated with the workpiece.

2. A system according to claim 1, where the cutting tool is at least one of a hand-held and a free-hand cutting tool.

3. A system according to claim 1, wherein the cutting tool includes at least one cutting element, and where the cutting element comprises at least one of: at least one blade, at least one rotatable blade, at least one retractable blade, at least one water jet, at least one particulate jet, at least one lithotriptor, and at least one ultrasonic lithotriptor.

4. A system according to claim 1, where the controller controls the cutting tool by providing a control to perform at least one of: at least partially retract at least one cutting element, and at least partially reduce a rotation rate of at least one cutting element.

5. A system according to claim 1, where the controller transmits a control signal to the cutting tool, where the control signal includes at least one of: an analog signal, a digital signal, and no signal.

6. A system according to claim 1, where the tracker includes tracking data based on at least three positions and at least three angles.

7. A system according to claim 6, where the at least one first marker and the at least one second marker comprise at least one of: at least one infrared source, at least one Radio Frequency (RF) source, at least one ultrasound source, and at least one transmitter.

8. A system according to claim 1, where the system further includes at least one image associated with the workpiece and at least one image associated with the cutting tool.

9. A system according to claim 8, where the at least one workpiece image is registered to the workpiece, and the at least one cutting tool image is registered to the cutting tool.

10. A system according to claim 1, further including means to register the workpiece to at least one image associated with the workpiece, and means to register the cutting tool to at least one image associated with the cutting tool.

11. A system according to claim 1, further including means to provide at least one image associated with the workpiece, and means to provide at least one image associated with the cutting tool.

12. A system according to claim 1, further including a means to transform the tracking data to at least one of: at least one workpiece image and at least one cutting tool image.

13. A system according to claim 1, wherein the workpiece comprises at least one of: bone, cartilage, tendon, ligament, muscle, connective tissue, fat, neuron, hair, skin, a tumor, and an organ.

14. A system according to claim 1, wherein the tacking system comprises at least one of: an infrared tracking system, an optical tacking system, an ultrasound tacking system, an inertial tracking system, and a RF tracking system.

15. A system according to claim 1, wherein the cutting tool comprises an endoscopic instrument.

16. A system according to claim 1, where the controller includes at least one of a collision detection module and an intersection detection module.

17. A system, comprising:
a workpiece having a target shape included therein,
a tracker to track at least one of: a cutting tool and the workpiece, and,
a control system, the control system including instructions to cause a processor to track the cutting tool and the workpiece, to associate the tracked data to an image associated with the cutting tool and an image associated with the workpiece, where the workpiece includes an image associated with the target shape, to determine a relationship between the cutting tool and at least one of the workpiece and the target shape, and to provide a control to the cutting tool based on at least one of the relationship of the cutting tool and the workpiece, and the relationship of the cutting tool and the target shape.

18. A system according to claim 17, further including an image registration means, where the image registration means registers the workpiece to an image associated with the workpiece, and the image registration means registers the cutting tool to an image associated with the cutting tool, and wherein,
the control system includes instructions to update at least positions of the workpiece image and the cutting tool image based on data from the tracker, and,
where at least one of the relationship of the cutting tool and the workpiece, and the relationship of the cutting tool and the target shape, are based on the updated image positions.

19. A system according to claim 18, where the relationship between the cutting tool and the workpiece is based on at least one of position data and angle data associated with at least one of the cutting tool and the workpiece, where the position data and angle data are based on the tracker.

20. A system according to claim 18, where the relationship between the cutting tool and the target shape is based on at least one of position data and angle data associated with at least one of the cutting tool and the target shape, where the position data and angle data are based on the tracker.

21. A system according to claim 17, where the instructions to determine a relationship include instructions to:
represent the workpiece as a group of volume pixels (voxels),
based on the tracker data, perform at least one of classify the voxels and update the voxels.

22. A system according to claim 21, where the instructions to classify voxels corresponding to the target shape include classifying voxels as target shape and classifying voxels as waste.

23. A system according claim 21, to where the instructions to classify voxels corresponding to the target shape include instructions to color-code voxels corresponding to the target shape.

24. A method, the method comprising:
providing a workpiece that includes a target shape,
providing a cutting tool,
providing a 4-D image associated with the workpiece,
identifying the target shape within the workpiece image,
providing a 4-D image associated with the cutting tool,
registering the workpiece with the workpiece image,
registering the cutting tool with the tuning tool image,
tracking at least one of the workpiece and the cutting tool,
transforming the tacking data based on image coordinates to determine a relationship between the workpiece and the cutting tool, and,
based on the relationship, providing a control to the cutting tool.

25. A method according to claim 24, where the workpiece image is comprised of volume pixels (voxels).

26. A method according to claim 24, further comprising representing the workpiece image using volume pixels (voxels), and classifying the workpiece image voxels based on the target shape.

27. A method according to claim 26, further comprising re-classifying the voxels based on the relationship.

28. A method according to claim 26, where classifying includes distinguishing between target shape voxels and workpiece voxels.

29. A method according to claim 28, where distinguishing includes associating target shape voxels with the target shape and associating non-target shape voxels as waste.

30. A method according to claim 28, where distinguishing includes color-coding at least target shape voxels associated with the target shape.

31. A method according to claim 26, where classifying includes,
identifying mixture voxels that include part workpiece and part target shape,
subdividing the mixture voxels, and,
iteratively returning to identifying mixture voxels to a predetermined voxel resolution.

32. A method according to claim 31, where subdividing the mixture voxels includes subdividing based on an octree.

33. A method according to claim 31, further comprising recombining voxels having the same classification.

34. A method according to claim 24, where providing an image associated with the workpiece includes providing at least one of: CT scan data, X-ray data, MRI data, fluoroscopy data, and ultrasound data.

35. A method according to claim 24, further including calibrating a probe.

36. A method according to claim 35, where at least one of registering the workpiece and registering the cutting tool includes employing the calibrated probe to identify at least one location on at least one of the workpiece and the cutting tool.

37. A method according to claim 24, where tracking includes providing at least one marker on at least one of the workpiece and the cutting tool.

38. A method according to claim 24, where tracking includes determining at least one position and at least one angle associated with at least one of the workpiece and the cutting tool.

39. A method according to claim 24, where transforming the tracking data includes performing at least one of collision detection and interference detection.

40. A method according to claim 24, where identifying includes classifying voxels associated with the workpiece based on the tracking data.

41. A method according to claim 26, where classifying includes re-classifying voxels based on the tracking data.

42. A method according to claim 41, where re-classifying includes identifying voxels associated with the workpiece that are eliminated by the cutting tool.

43. A method according to claim 41, where at least one of classifying and re-classifying includes,
identifying mixture voxels,
subdividing the mixture voxels, and,
iteratively returning to identifying mixture voxels, until reaching a predetermined voxel resolution.

44. A method according to claim 43, where identifying mixture voxels includes identifying voxels having more than one classification.

45. A method according to claim 43, where subdividing the mixture voxels includes subdividing based on an octree.

46. A method according to claim 43, further comprising recombining voxels having the same classification.

47. A method according to claim 24, where providing a control includes determining a distance between the cutting tool image and the target shape.

48. A method according to claim 24, where providing a control includes increasing the size of the cutting tool image to determine whether the increased size cutting tool image intersects with the target shape in the workpiece image.

49. A method according to claim 48, where increasing the size includes at least one of increasing the size by a fixed amount, and increasing the size based on tracking data associated with the cutting tool.

50. A method according to claim 24, where providing a control includes providing a control based on the relationship between a cutting element associated with the cutting tool image, and voxels classified based on the target shape.

51. A method according to claim 24, where providing a workpiece image comprises,
providing a three-dimensional grid of voxels,
incorporating the workpiece image into the grid, and,
identifying grid voxels associated with the workpiece.

52. A method according to claim 51, where identifying grid voxels associated with the workpiece includes associating at least one of the grid voxels with at least one of the workpiece and the target shape.

53. A method according to claim 24, where providing a control includes at least one of: providing an analog signal, providing a digital signal, providing a control to at least partially retract a cutting element associated with the cutting tool, providing a control to reduce the speed of a cutting element associated with the cutting tool, and providing a control to stop a cutting element associated with a cutting tool.

54. A method according to claim 24, where providing a control to the cutting tool, includes performing at least one of collision detection and intersection detection.

55. A method according to claim 24, where providing a control to the cutting tool includes performing at least one of collision detection and intersection detection between at least part of the cutting tool and the target shape of the workpiece image.

56. A method according to claim 24, where identifying the target shape includes classifying voxels associated with the workpiece image as at least one of workpiece and target shape.

57. A method according to claim 55, where providing control to the cutting tool includes performing at least one of collision detection and intersection detection between at least part of the cutting tool and the target shape voxels.

58. A method according to claim 24, where providing a control includes providing a control based on a threshold distance between the workpiece image and the cutting tool image.

59. A system, comprising:
a free-hand cutting tool;
a controller in communications with the cutting tool and to control the cutting tool based on the position of the cutting tool relative to a target shape.

60. A system according to claim 59, where the cutting tool is a hand-held cutting tool.

61. A system according to claim 59, where the target shape is associated with a workpiece.

62. A system according to claim 59, further comprising a tracker to provide tracking data associated with the cutting tool and the workpiece.

63. A system according to claim 62, where the controller is based on the tracking data.

64. A system according to claim 59, where the control includes at least one of: at least partially retract at least one cutting element associated with the cutting tool, and at least partially reduce a rotation rate of at least one cutting element associated with the cutting tool.

65. A system according to claim 59, where the target shape includes a bone.

* * * * *